(12) United States Patent
Pesce

(10) Patent No.: US 11,713,473 B2
(45) Date of Patent: *Aug. 1, 2023

(54) PROCESS FOR ACCELERATING, INCREASING, AND STABILIZING PRODUCTION OF BIOGAS WITH A HIGH METHANE CONTENT IN SYSTEMS FOR ANAEROBIC BIODIGESTION OF ORGANIC WASTES

(71) Applicants: G-Meta Consultoria, Participações e Serviços LTDA, Rio de Janeiro (BR); Bio-Tronic Energy Co. LLC, Berkeley, CA (US)

(72) Inventor: Luciano Pesce, Casella (IT)

(73) Assignees: G-Meta Consultoria, Participações e Serviços LTDA, Rio de Janeiro (BR); Bio-Tronic Energy Co. LLC, Berkeley, CA (US)

( * ) Notice: Subject to any disclaimer, the term of this patent is extended or adjusted under 35 U.S.C. 154(b) by 85 days.

This patent is subject to a terminal disclaimer.

(21) Appl. No.: 17/365,619

(22) Filed: Jul. 1, 2021

(65) Prior Publication Data
US 2021/0324422 A1 Oct. 21, 2021

Related U.S. Application Data

(63) Continuation of application No. 14/373,094, filed as application No. PCT/BR2013/000051 on Feb. 25, 2013, now Pat. No. 11,085,058.

(30) Foreign Application Priority Data

Mar. 2, 2012 (BR) .......................... 1020120047500

(51) Int. Cl.
*C12P 5/02* (2006.01)
*C12M 1/107* (2006.01)
*C12M 1/36* (2006.01)

(52) U.S. Cl.
CPC ............. *C12P 5/023* (2013.01); *C12M 21/04* (2013.01); *C12M 41/48* (2013.01); *Y02E 50/30* (2013.01)

(58) Field of Classification Search
None
See application file for complete search history.

(56) References Cited

U.S. PATENT DOCUMENTS 11,085,058 B2 * 8/2021 Pesce .................... C12M 41/48

* cited by examiner

*Primary Examiner* — Vera Afremova
(74) *Attorney, Agent, or Firm* — Li & Cai Intellectual Property (USA) Office

(57) ABSTRACT

The present disclosure discloses a process for accelerating, increasing, and stabilizing production of biogas with a high methane content in systems for biodigestion of organic waste. The process comprises: a) obtaining from an anaerobic biodigester (3) a fraction of organic waste equal in weight to K times the weight of the daily organic waste load of the anaerobic biodigester (3), wherein the parameter K is a numeric value selected between $10^{-3}$ and $10^{-1}$, sending the fraction to one or more acceleration devices (4), retaining the fraction in the one or more acceleration devices (4) until a final concentration (Cf) of the methanogenic bacteria in the fraction is equal to M times an initial concentration (Ci), wherein the parameter M is a numeric value selected between $10^3$ and $10^8$; b) as soon as said final concentration (Cf) is obtained in the fraction, directing said fraction from the acceleration device (4) back to the anaerobic biodigester (3); and c) successively repeating steps a) and b).

9 Claims, 5 Drawing Sheets

PROCESS FOR ACCELERATING, INCREASING, AND STABILIZING PRODUCTION OF BIOGAS WITH A HIGH METHANE CONTENT IN SYSTEMS FOR ANAEROBIC BIODIGESTION OF ORGANIC WASTES

CROSS-REFERENCE TO RELATED APPLICATIONS

The present application is a continuation of U.S. patent application Ser. No. 14/373,094, filed on Jul. 18, 2014, which is based on International Application No. PCT/BR2013/000051, filed on Feb. 25, 2013, which claims priority to Brazilian Patent Application No. 1020120047500, filed on Mar. 2, 2012; the entire contents of these applications are incorporated herein by reference.

TECHNICAL FIELD

The invention refers to a process for accelerating, increasing, and stabilizing production of biogas with high methane content in anaerobic biodigestion plants. The biogas may successively be employed in the generation of electric and thermal energy, or for other purposes such as synthesis of methanol or other compounds, among other applications.

The process is based upon the use of biotechnologies, hardware, and software specifically developed for this aim. The acceleration system stimulates and stabilizes biologically the production of autochthonous methanogenic bacteria, originally contained in the substrate material to be processed, through repeated cycles of withdrawing a small fraction of organic material from the anaerobic biodigester, greatly multiplying its concentration of methanogens in a controlled microenvironment in an off-line bio-accelerator, and returning the enriched fraction to the anaerobic biodigester. This process increases the concentration of methanogens in the entire organic waste product in the biodigester and accelerates and stabilizes the anaerobic digestion process therein, thereby increasing the quantity of the biogas produced and of the percentage of methane contained in this biogas. The process is managed by an automation expert system, which controls the biological, chemical and physical variables to achieve these results.

BACKGROUND

The process of anaerobic biodigestion is widely known, studied, and employed since antiquity, mainly in the treatment of civil sewage, agricultural wastes, and wastes from cattle and pig breeding. Each waste has a potentiality of production of biogas, depending on the percentage of volatile solids contained in that specific waste. Literature presents several tables on this subject, expressing the potentiality in terms of cubic meters of biogas produced for each ton of waste processed ($m^3$/ton). Anaerobic biodigestion is now considered a sustainable way to dispose of wastes, producing a certain amount of energy as a byproduct.

The percentage of methane contained in the biogas typically falls within a range 55% to 70%. The higher level rarely is achieved in practice due to the difficulty of controlling the biodigestion process, which develops partly in a spontaneous way, reaching an average 70% of its potential during the time needed for the biodigestion (on average 30 to 40 days).

Several systems have been developed and patented, depending on their process technologies, mainly relating to the dry, semi-dry, wet, or other particular state in which the organic wastes are processed in the digesters. Independent of the technological progress, what mainly has been considered during years of research and applications is the disposal of organic polluting wastes, as a primary purpose of the biodigestion systems, with energy production remaining a secondary aim.

The main achievements and improvements for the production of energy have been related to:

1. Increase of bacterial activity through the addition to the digesters of organic material different from the basic substrate, frequently agricultural material such as corn.
2. Addition of nutrients, through a dosing system with timer, for balancing the relative proportions of Carbon, Nitrogen, and Phosphorus (C:N:P).
3. Addition of enzymes, bacteria, or biotechnological products, often imported from other regions or countries.
4. Automation Systems addressing only the mechanical and electronic components of the plants (e.g., pumps, throttles, motors, automation, instruments, etc.).

REFERENCES

Bibliography

ANGELIDAKI, I.; Ellegaard, L. & Ahring, B. K., (1999) A comprehensive model of anaerobic bioconversion of complex substrates to biogas, Biotechnology and Bioengineering, 63: 363-372

BOUALLAGUI, H.; Landheb H.; Ben Romdan, E.; Rachdi, B. & Hamdi, M. (2009) Improvement of fruit and vegetable waste anaerobic digestion performance and stability with co-substrates addition, Journal of Environmental Management, 90: 1844-1849

BRAUN, R.; Weiland, P. & Wellinger, A. (2009) Biogas from Energy Crop Digestion, IEA Bioenergy, Task 37

FERNANDO LUCIANO MERLI DO AMARAL (2004) Biodigestão dos residuos sólidos urbanos: um panorama tecnológico atual, Instituto de Pesquisas Tecnológicas do Estado de São Paulo LOPO JOSÉ INFANTE DA CÂMARA LOPO CARVALHO (2010) Avaliação do potencial de produção de biogás a partir de biomassa proveniente de culturas dedicadas de ETARI, Instituto Superior de Agronomia Universidade Técnica de Lisboa DANIELE OLMETTO (2008) Codigestione anaerobica di fanghi di depurazione e frazione organica de R.U., Alma Mater Studiorum—Università di Bologna Facoltà di Ingegneria Corso di Laurea in Ingegneria per l' Ambiente e it Territorio—Tesi di Laurea in Ingegneria Sanitaria Ambientale LS Patents PATENTE MU 8502073-7U—Data de Depósito Sep. 16, 2005 Data de Publicação: May 29, 2007 (RPI 1899)

PATENTE PI01000529-3 A2—Data de Depósito Feb. 25, 2010 Data de Publicação: Oct. 10, 2011 (RPI 2128)

PATENTE PI0617206-7 A2—Data de Depósito Sep. 15, 2006 Data de Publicação: Jul. 19, 2011 (RPI 2115)

PATENTE PI 0600734-1 A—Data de Depósito Mar. 6, 2006 Data de Publicação: Nov. 20, 2007 (RPI 1924)

PATENTE PI 1000523 A2—Data de Depósito Feb. 25, 2010 Data de Publicação: Oct. 18, 2011 (RPI 2128)

EP 2248886 A2

U.S. Pat. No. 5,942,116

U.S. Pat. No. 4,274,838

US 2010/0159571A1

SUMMARY OF THE DISCLOSURE

The main problems of the state of the art applications described or listed above are summarized below:

Solutions described in points 1 and 2 above, involve increased costs for the nutrients or agricultural additives such as corn, in the latter case including longer retention times in the digesters.

Solutions described in point 3, which offer up to a 30% increase in production through the addition of allocthonous bacteria and enzymes to the biomass in the digesters, add costs for those materials and, if the materials are imported from other regions or countries, entail a certain risk in terms of bio-security, to the extent that import-export rules may regulate or restrict access to them, and environmental authorities are reluctant to grant the related authorizations.

Solutions at point 4 have had reduced efficacy due to limited control of the biological balance and the absence of a process management approach specifically devoted to optimization of biogas production.

Time for the completion of the biodigestion process, on average 30-40 days, must be considered. This requires biodigesters now in use to have a large volume, as biodigester volumetric capacity must be equal to the volume of the daily biomass loaded into the biodigester multiplied by the number of days needed for the completion of the biodigestion process. Apart from the cost increase involved in constructing a larger biodigester, one must consider the additional time and cost required to restart a larger biodigestion plant in case of a system collapse or interruption, where the restart might be able to proceed only after complete drainage of the biodigester.

Finally one must consider that solutions giving priority to the reduction of polluting loads of the waste material being treated in the biodigester in order to comply with laws and regulations generally end up producing a low quality compost, due to the presence of incompletely digested fractions.

Solutions in a General Way

The starting point for the invention presented here is an inversion of the classical approach to anaerobic biodigestion, which has considered the disposal of polluting wastes as a priority. In this way, the process has been directed mainly toward the reduction of polluting loads of wastes to meet existing legal requirements, without paying much attention to taking full advantage of the energetic potential of the wastes being treated.

In this invention priority is given to realizing the full energetic potential of wastes by increasing production of biogas and energy as much as possible. In considering extraction of the full energetic potential of wastes, advanced management of the entire biodigestion process becomes a priority, focusing on increase and stabilization of the quality and quantity of the biogas produced in that process.

Considering any kind of organic waste and its energetic potential as related in scientific literature, and as confirmed in research, and field test applications, the system invented makes possible an increase and acceleration of a biodigester's methanogenic process and its stabilization in time. To achieve these goals, the system invented borrows a fraction of organic material equal in weight to a small percentage of the host biodigester's daily organic waste load, analyzes its properties including, among others, its biomethane potential and its bacterial populations, and treats the fraction intensively in one or more watertight tanks (reactor vessels) in one or more offline bio-acceleration devices. The system involves real-time monitoring of the bio-acceleration process, analysis of its ongoing changes, and application of recipes for accelerating and increasing population growth of methanogenic bacteria in each type of organic waste, where the recipes (developed through simulation of the digestion process) consider the activity of methanogens in that specific process, the nutrients balance, and other process variables such as pH, temperature, and pressure, among other parameters of the managed microenvironment within the bio-accelerator's watertight tank. An Expert System monitors that microenvironment and intervenes successively in the bacterial processes responsible for the methanogenesis, as well as in all the other physical-chemical variables of the process, through a hardware-software system that accelerates and increases those processes, stabilizing at the same time the microbiological activity. Once the concentration of methanogens in the fraction of organic material being cultured in the bio-accelerator has been multiplied by a factor of $10^3$-$10^8$, it is sent back to the anaerobic biodigester system and mixed with its contents. This cycle of withdrawing a small fraction of organic material from the anaerobic biodigester, greatly multiplying its concentration of methanogens in a controlled microenvironment in an off-line bio-accelerator, and returning the enriched fraction to the anaerobic biodigester is then repeated continuously, thereby increasing the concentration of methanogens in the entire organic waste product in the biodigester and accelerating and stabilizing the anaerobic digestion process therein. These effects can be increased if the information about the optimal conditions for growth of the methanogens determined by the Expert System through monitoring and control of the microenvironment in the bio-acceleration device are applied to control the environment in the host biodigester, through manual interventions by the operators of the biodigester or through direct interaction between the Expert System of the acceleration device and the automated control system of the biodigester.

In summary, the accelerated biodigestion process achieves the objective of the invention presented here by enabling the anaerobic biodigester to take full advantage of the volatile solids contained in each substrate of the organic material in the biodigester feed. Biogas production can be increased by 10% or more, while methane content can be increased by as much as 15 percentage points, from an average of around 60% in a traditional biodigester to as much as 75% in a biodigester enhanced by an acceleration device system. The acceleration of the digestion process can also reduce the residence time of the material in the biodigester by as much by around 30%-40%, allowing a similar reduction of the size of a biodigester system if designed to incorporate use of the invention presented here as an integral component.

Figure 1:
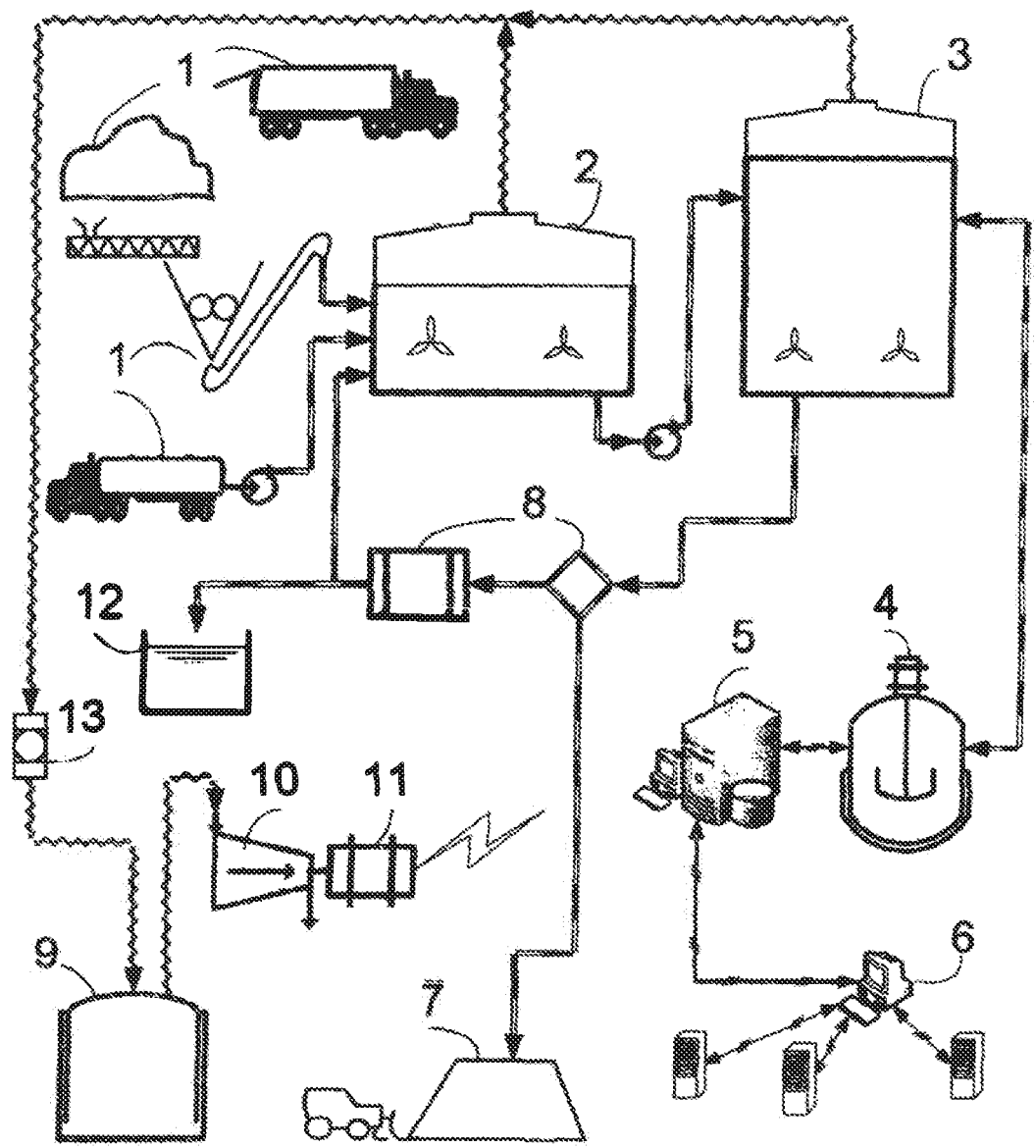
FIG. 1 is a flow diagram illustrating the process for accelerating and increasing biogas production, with high methane content in anaerobic biodigestion plants, which is the object of the present invention, according to an example embodiment of the present invention applied to a typical anaerobic biodigestion plant.
Figure 2:
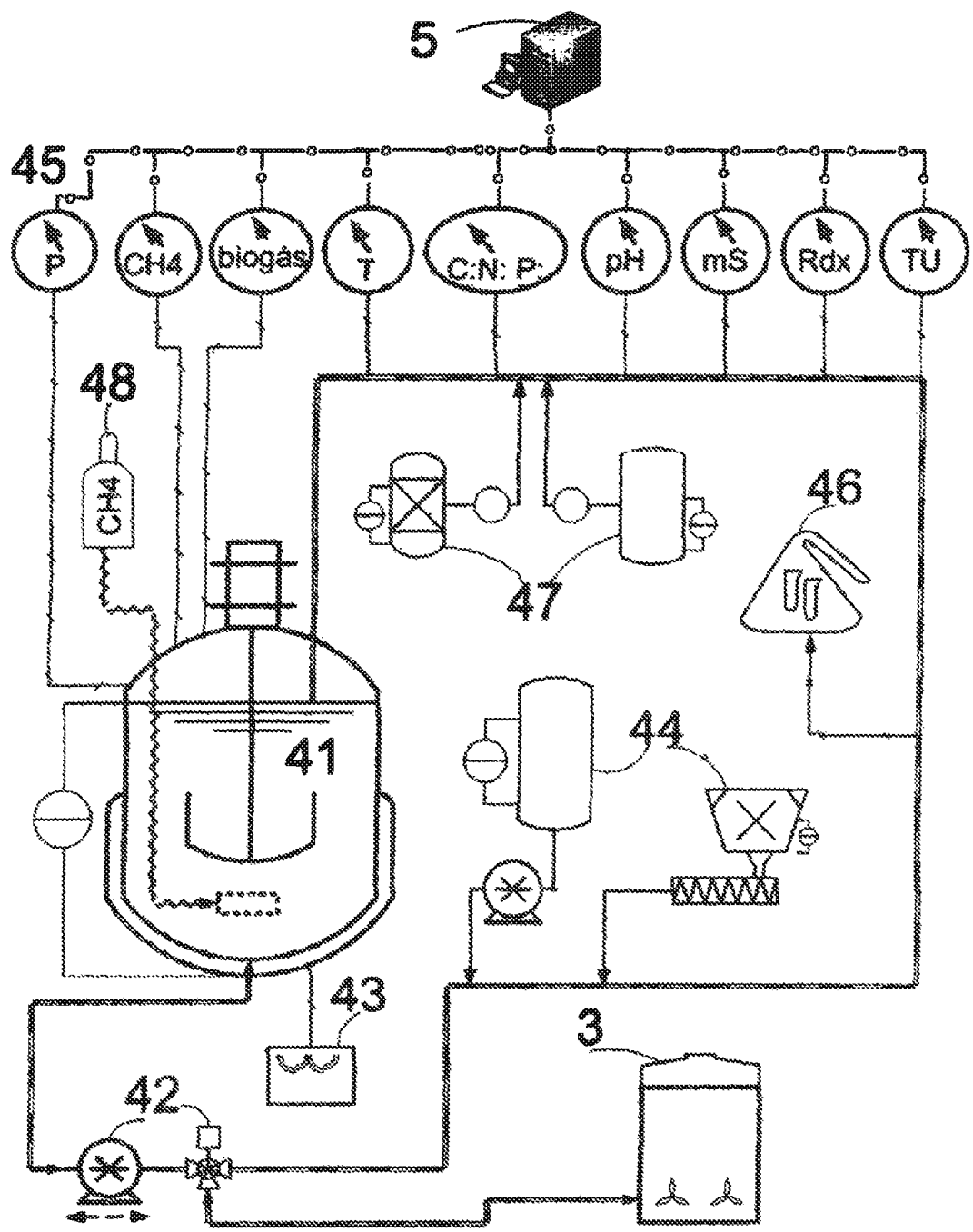
Figure 3:
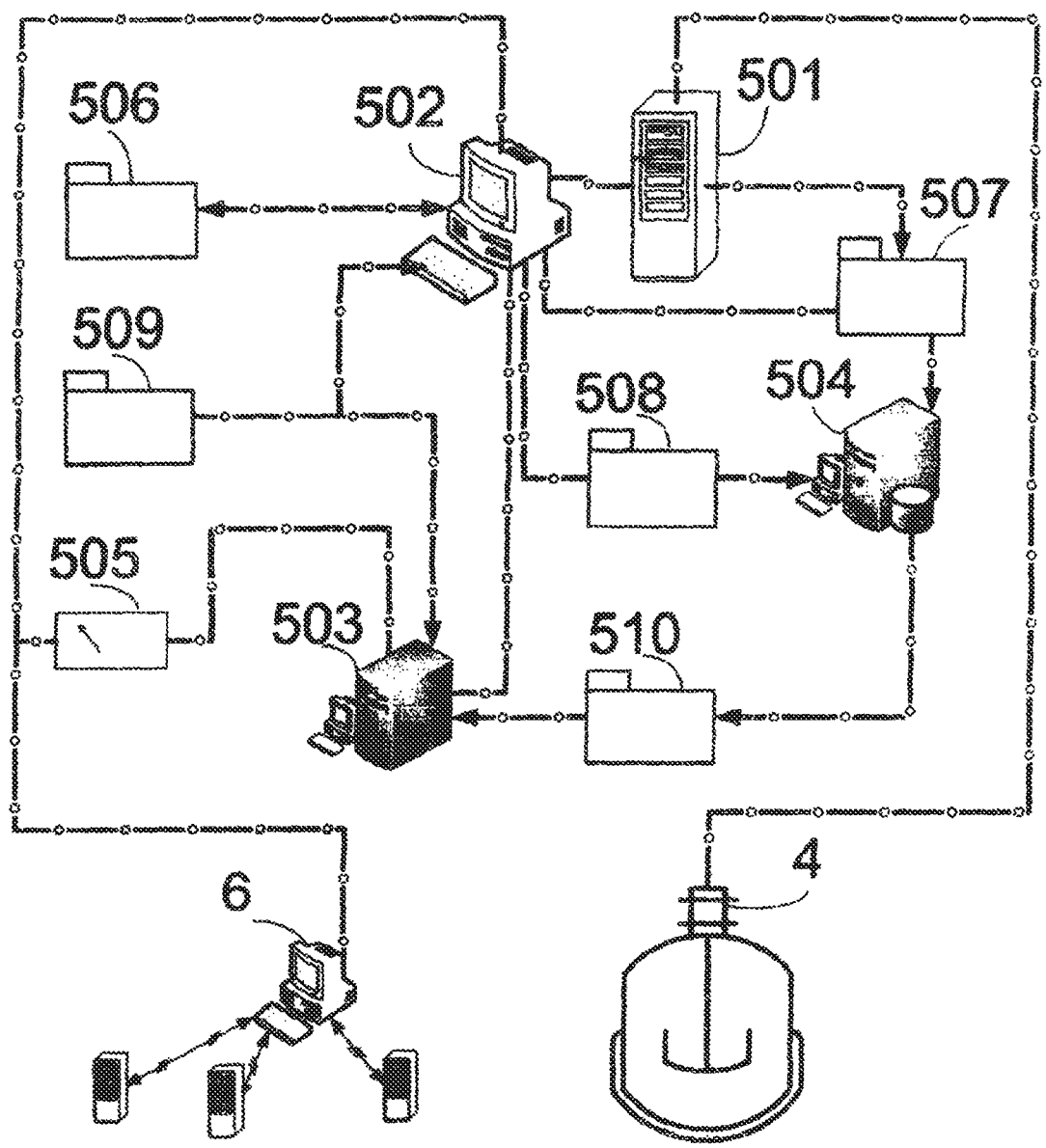

1 represents Organic Wastes, that feed the Anaerobic Biodigester plant;

2 represents an Accumulation Mixer/Homogenizer for pre-processing Organic Wastes for the Anaerobic Biodigester plant;

3 represents an Anaerobic Biodigester;
4 represents an Acceleration Device;
5 represents an Expert System monitoring and controlling the Acceleration Device, including the process by which multiplication of methanogenic bacteria is accelerated, and, optionally, the host anaerobic biodigestion plant;
6 represents a Plant Automation and Control System;
7 represents Compost;
8 represents a Waste Water Treatment Plant (WWTP) and Slurry Treatment Plant treating the plant's effluents;
9 represents Biogas;
10 represents Turbines or Motors;
11 represents a Generator;
12 represents a Treated Water Tank;
13 represents a Biogas Filter;

FIG. 2 is a diagram illustrating an acceleration device shown in FIG. 1;

41 represents a Watertight Tank in the Acceleration Device;
42 represents Means for mixing, withdrawal and re-introduction of the daily load fraction treated in the Acceleration Device;
43 represents Means for temperature control;
44 represents Means for the introduction of additives and nutrients;
45 represents Monitoring Sensors for:
  Pressure (P)
  Methane Percentage (CH4)
  Biogas flow
  Temperature (T)
  Parts-per-million (PPM) of carbon, nitrogen and phosphorus (C:N:P)
  Acid-base degree (pH)
  Electrical conductivity (mS)
  Oxyreduction (Rdx)
  (TU)
46 represents Means for biological sampling and analysis;
47 represents Tanks for chemical substances for pH control;
48 represents Methane Storage Tank;

FIG. 3 is a diagram illustrating the functional schematic of an Expert System, which monitors and controls the Acceleration Device, including the processes by which multiplication of methanogenic bacteria is accelerated, and, optionally, the host anaerobic biodigestion plant, leading to increased biogas production, with high methane content, in the anaerobic biodigestion plant;

501 represents PLC Programmable Logic Controller and electric automation of the Acceleration Device (4);
502 represents Main Control Station;
503 represents Server of programs and mathematical models;
504 represents Database Server;
505 represents Interface with Automation and Control System (6) of the whole plant;
506 represents Connection and automation program;
507 represents Monitoring Programs;
508 represents Recipes elaboration programs;
509 represents Input data for the Expert System; and
510 represents Database elaboration programmes.

Figure 4:
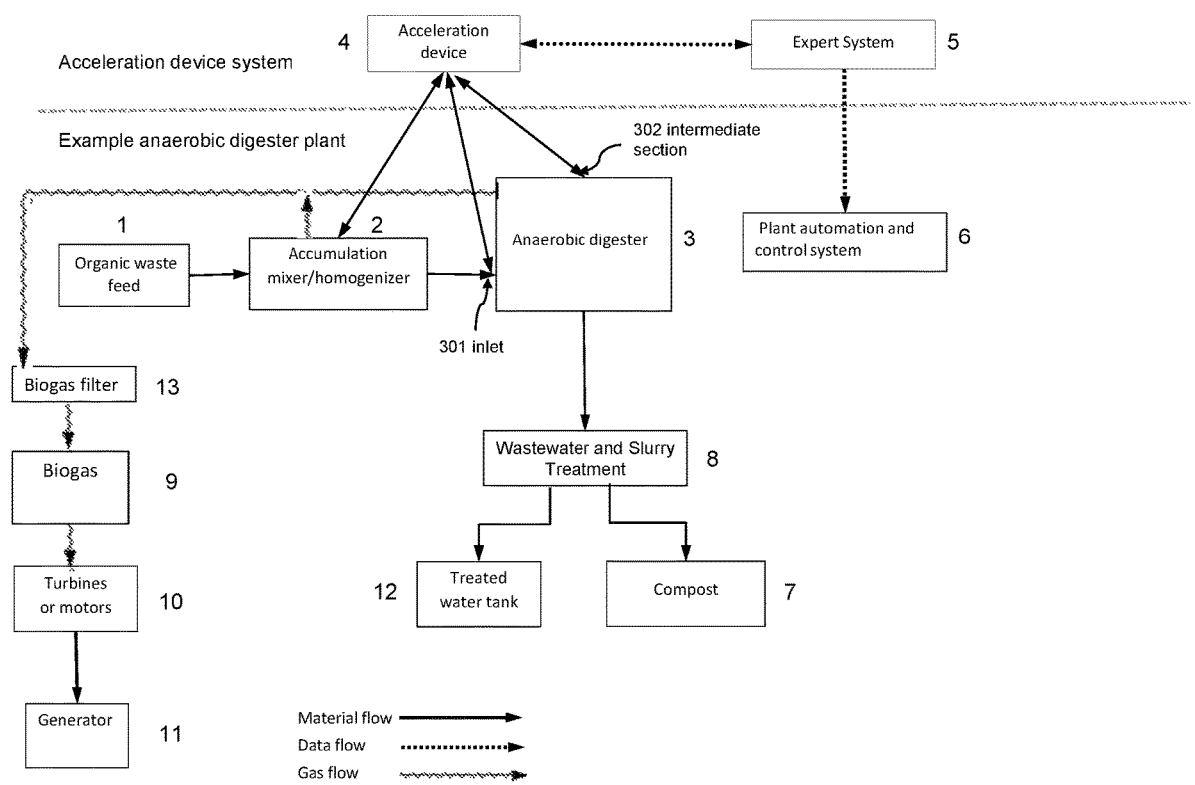
Figure 5:
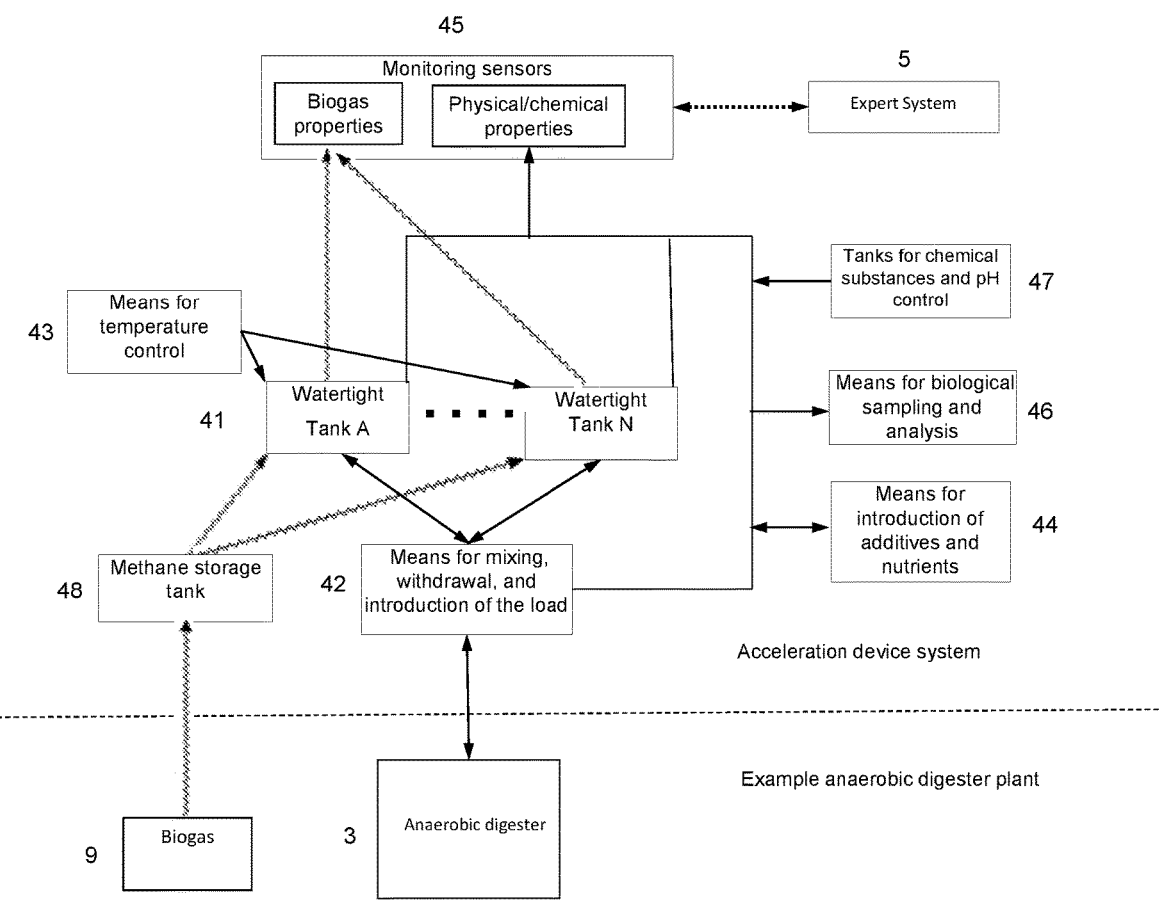

FIG. 4 is a diagram illustrating the process of increasing biogas production, with high methane content, in anaerobic biodigestion plants, according to another example embodiment of the present invention; and FIG. 5 is a diagram illustrating the structure and flows in an embodiment of the acceleration devices shown in FIG. 1 and FIG. 4.

In the FIGS. 1-3, lines broken with dots and diagonal slashes represent electrical connections with data flows; lines with overlapped waves show gas paths; continuous lines represent functional service connections; thicker black-and-white-dashed lines represent flows of materials. In the FIGS. 4 and 5, as indicated in a legend for each figure, fine-dotted lines represent electrical connections with data flows; lines with overlapped waves show gas paths; continuous lines represent functional service connections; and thicker solid lines represent flows of materials.

DETAILED DESCRIPTION OF THE INVENTION

Referring to the example biodigestion plant enhanced by an acceleration device shown in FIG. 1 and FIG. 4, Organic Wastes (1) are loaded in the Accumulation Mixer/Homogenizer (2), in order to homogenize the load and create an accumulation storage equal to 3 or 4 days of daily load, able to guarantee the continuous feeding of Anaerobic Biodigester (3), that will be of the type most appropriate to treat that kind of input Organic Wastes (1), although possibly having a total volume about 30%-40% smaller than digesters employed in traditional plants if the plant is designed to take advantage of the reduction of retention time of the process made possible by the acceleration induced in the multiplication of methanogenic bacteria realized by the combined action of the Acceleration Device (4) and Expert System (5). In the Accumulation Mixer/Homogenizer (2), the preliminary hydrolytic phase occurs, preceding successive acidogenic and methanogenic phases that occur thereafter inside the Anaerobic Biodigester (3).

From the Anaerobic Biodigester (3) we obtain, respectively, Biogas (9) with high methane content, collected in and drawn off from the upper space beneath the Anaerobic Biodigester (3) cover and, in the outlet section, wastewater, slurry, and Compost (7), after they are separated in the Wastewater Slurry and Treatment Plant (WWTP)(8).

Biogas (9), thus obtained, is cleaned of corrosive contaminants by the Biogas Filter (13), before being sent for multiple possible end uses, including, for example, as fuel for providing process heat, or driving industrial or vehicular motors, or turbines (10) to operate a Generator (11), or to send for further refinement to commercial pipeline standards. Water separated from Compost (7) that leaves the Anaerobic Digester (3) is treated by the WWTP and Slurry Treatment Plant (8) and stored in the Treated Water Tank (12).

A Plant Automation and Control System (6), under the supervision of the Expert System (5), optionally allows automated management of the plant.

Acceleration of the multiplication of methanogenic bacteria is realized according to the following sequence:

a) a fraction equal in weight to K times the daily load of the Anaerobic Biodigester (3), collected in whatever manner, is sent to one or more Acceleration Devices (4) for treatment for the multiplication of methanogenic bacteria present in the Organic Wastes (1) and there it remains until the final concentration Cf of those bacteria in that collected fraction is equal to M times the initial concentration Ci.

b) once the final concentration Cf of methanogenic bacteria is obtained, the collected fraction leaves the Acceleration Device (4) to be redirected to the Anaerobic Digester (3), preferably, but not exclusively, in the inlet section of the same Anaerobic Digester (3), where it is mixed and distributed inside the whole lot of daily load.

c) Successive cycles of duration D of the above-mentioned operations described at a) and b) are repeated, with K parameter assuming a value comprised between $10^{-3}$ and $10^{-1}$, with M parameter assuming a value comprised between $10^3$ and $10^8$ and with D parameter varying between 8 and 24 hours.

Referring to FIG. 2 and FIG. 5, according to the invention, the Acceleration Device (4) is constituted by one or more Watertight Tanks (41), where a methane atmosphere is induced and where the following items are included:

a) Means for mixing, withdrawal and re-introduction of the load (42).

b) Means for the temperature control (43), such as to guarantee a temperature within the accelerator between 20° C. and 65° C.

c) Means for the introduction of additives and nutrients, so as to guarantee the desired balance of Carbon, Nitrogen and Phosphorus (44).

d) Means (45) for measuring and analyzing Temperature (T), Pressure (P), Methane Percentage (CH4), Biogas flow (biogas), PPM of carbon, nitrogen and phosphorous (C:N:P), acid-basic degree (pH), Electrical conductivity (mS), Oxyreduction (Rdx), and Turbidity (TU).

e) Means for biological sampling and analysis (46), able to measure the bacteria development and concentrations.

f) Tanks for chemical substances for pH control (47), between 5 and 8.

g) Methane Storage Tank (48), which can be fed by the biogas produced by the plant, previously filtered.

Operations, regulations, measurement and controls mentioned above and described in better detail further on, are meant for the creation of a microenvironment ideal for the accelerated reproduction of autochthonous methanogenic strains already present in the Organic Wastes (1).

As a matter of fact, by working with a reduced fraction of the wastes to be treated, in a totally controlled environment, it becomes much easier to drive the biological process in the desired direction. Consider, as an example, a medium-size biodigestion plant treating 100 tons/day of Organic Wastes (1), from which is sent to the Acceleration Device (4) a fraction equal in weight to 1% of the daily load, namely one ton of Organic Wastes (1) which, having a density close to that of water, is equivalent to a cubic meter within the Acceleration Device (4). This is a much easier environment to control compared to that of a host Anaerobic Digester (3) that, in the case of a traditional plant, would have a volume of 3000 cubic meter (30 days×100 cubic meters per day), 3000 times greater than would be required for the Watertight Tank (41) of the Acceleration Device (4) designed to accommodate a one cubic meter fraction of organic material.

Through the Means for mixing (42), for pH Control (47), and for Temperature control (43) of the microenvironment in the Watertight Tank (41) of the Acceleration Device (4), hydrolysis and acidogenesis of the fraction of Organic Wastes can be accelerated, both of which are phases preliminary to the disaggregation of complex molecules of proteins, fats and carbohydrates composing the Organic Wastes (1).

Those phases are preliminary to the methanogenesis phase, which occurs through the action of several methanogenic bacteria within the substrate. These methanogenic bacteria find themselves in competition with other bacterial strains (aerobic, anaerobic, and facultative), and are present in the fraction of Organic Wastes (1) at an initial concentration (Ci) that is relatively low (some thousands per gram).

Thanks to the bubbling of methane coming from the Methane Storage Tank (48), which is introduced in the Watertight Tank (41) counter to the flow of the material being processed therein, and thanks to the addition of Nutrients (47) needed for the balance of Carbon, Nitrogen, and Phosphorus (in a quantity 3000 times less than what would be needed to add to the traditional Anaerobic Biodigester (1) to obtain the same effect), an environment is created that is remarkably favorable to the development of the autochthonous methanogenic bacteria present. In these conditions, the methanogenic bacteria can multiply themselves rapidly within the fraction in the Watertight Tank, reaching a final concentration (Cf) close to one billion per gram in relatively short times, depending on the substrates used and on the environmental conditions created.

The control of the proliferation rate of the methanogenic strains is realized by a series of sensors (45) as described above, along with the use of biological sampling and analysis (46), able to measure the bacteria development and concentrations.

In the example described above [0100] with an initial concentration Ci=5000 of methanogenic bacteria per gram in the fraction of Organic Waste and a final concentration Cf=500,000,000 bacteria per gram, detected by appropriate means of biological sampling and analysis (46), it can be deduced that through the Acceleration Device (4) a multiplication factor M equal to 100,000 for the concentration of methanogenic bacteria can be obtained.

Continuing this example, when the 1 ton fraction of Organic Wastes (1), treated and enriched in the Acceleration Device (4), is returned to the Anaerobic Biodigester (3), preferably through the inlet section, and is mixed with the 99 tons of daily load from which it had been extracted, the very high concentration of methanogens in the 1 ton fraction is diluted by the other 99 tons of unenriched material. As a result, the effective multiplication factor of bacteria in the total daily load (Mr) is simply the multiplication factor in the enriched fraction (M) reduced by the ratio of the size of the fraction of enriched material to the size of the daily load (K). That is, Mr=M (100,000)×K (0.01)=1000. This means that autochthonous methanogenic bacteria living in that daily load have become 1000 times more numerous in relation to the original concentration, which increases the Biogas (9) production in the anaerobic biodigester and at the same time increases the percentage of methane contained in it.

At this stage, new cycles of biomass withdrawal, treatment and enrichment in the Acceleration Device, and, once potentiated, successive re-introduction to the Anaerobic Digester (3), are initiated.

According to another example embodiment of the present invention as shown in FIG. 4, the fraction of organic waste equal in weight to K times the weight of the daily organic waste load of the anaerobic biodigester (3) can be withdrawn also from the intermediate sections (302) of the Anaerobic Biodigester (3) and re-directed, once potentiated, to the inlet section of the Anaerobic Biodigester (3) as well as to the other section.

Moreover, according to another example embodiment of the present invention as shown in FIG. 4, in the initial phase of the loading of the plant a fraction equal to K times the daily load of the Anaerobic Biodigester (3) may be obtained directly from the accumulation mixer/homogenizer (2) and successively re-introduced, potentiated, to the same point or to the inlet section of the Anaerobic Biodigester (3).

In relation to FIG. 3, the sequence of operations related to the functioning of the Acceleration Device (4) is realized automatically through an Expert System composed of:

a) A Programmable Logic Controller (PLC) and electric automation (501) of the Acceleration Device (4).

b) A Main Control Station (502) where the supervision of the Acceleration Device (4) is realized, with the visualization of synoptical controls of the latter and, optionally, of the whole plant through the Plant Automation and Control System (6).

c) A Server for programs and mathematical models (503), where all programs related to the management development are installed.

d) A Database Server (504), containing a database for the control of a microenvironment for accelerated multiplication of the autochthonous methanogenic bacteria in the Watertight Tank (41) of the Acceleration Device.

e) An Interface (505) with the Automation and Control System (6) of the Anaerobic Biodigester (3) and, optionally, of the whole plant.

f) A Connection and automation program (506), which allows connections with the different parts of the Automation and Control System (6).

g) Monitoring Programs (507) that enable the online transformation, visualization, and recording of process data.

h) Recipes elaboration programs (508) that allow elaboration in the Database of recipes obtained from the evolution curves of parameters measured by instruments (45), subject to the dosing actuators, and also from laboratory data and data from other plants.

i) Input data for the Expert System (509), which can be local (via operator) or remote.

j) Database elaboration programs (510) that manage data in the server and organize them in according to the demands of the above-mentioned programs.

The architecture here described allows the complete control of the multiplication process of the autochthonous methanogenic bacteria within the Acceleration Device (4).

Algorithms derived from the analysis of trends allow parameters, with the help of Fuzzy Logic modeling, to be directed automatically to the commands that respond to the necessities of the process.

Even on the basis of approximated input data, the system can perform auto-correction, automatically promoting the adjustments the methanogenic process requires.

For example, the system understands through recipes and mathematical models that multiplication is advancing if:

Turbidity increases
pH is between 5 and 6.8
Percentage of methane [CH4] rises
Biogas flow rises
Temperature is in the ideal range for that stage
Etc.

The Expert System (5) also can control, optionally, through the Main Control Station (502), the Automation and Control System (6) of the Anaerobic Biodigestion Plant through the Interface (505) with it, to force the alignment of parameters inside the Anaerobic Biodigester (3) favorable to the accelerated reproduction of the methanogenic bacteria, supporting the same conditions in the Anaerobic Biodigester (3) as created in the microenvironment inside the Acceleration Device (4). This can increase biogas production (9) of the Anaerobic Biodigester (3) and the methane percentage contained in it beyond what can be achieved simply by providing regular doses of digestate enriched with high concentrations of methanogens to the Anaerobic Biodigester from the acceleration device.

The operator can follow the development of the process and of the automation on the screens of the Main Control Station (502).

In case of new situations occurring, not contemplated by actual software configuration, the operator will be able to manually intervene and the system will record the new operation automatically.

According to the present invention the Expert System (5) can take advantage of the analysis and parameters detected during the monitoring of the biodigestion process to formulate recipes for the correction of Compost (7) extracted from the Anaerobic Biodigester (3), in order to increase its fertilizing power.

According to the present invention the Expert System (5) has the capability to take advantage of the analysis and parameters detected during the monitoring of the biodigestion process in order to regulate the WWTP and Slurry Treatment Plant (8) so as to make more efficient the production of water entering the Treated Water Tank (12).

The Turbines or Motors (10) shown in FIG. 1 have cooling circuits (omitted in the figure for simplicity) that allow the use of thermal energy, in cogeneration, for appropriate heating of the Anaerobic Biodigester (3) and, in trigeneration by heat pumps, to feed air conditioning systems. The increased extraction of methane from the operation of the biodigester resulting from the application of the present invention can increase the economic feasibility of such use of otherwise wasted heat.

Biogas (9) produced can also be treated to produce methane very similar to natural gas that can be used instead of natural gas in domestic, industrial, or vehicular applications. The increase in the methane content of the biogas produced by the Anaerobic Biodigester resulting from the application of the invention presented here (from the average 60% of methane in a traditional plant to around 75% in a bio-accelerated system) reduces the cost and difficulty of further refinement of the biogas to be considered a natural gas equivalent (biogas refined up to 97-99% methane content).

While the described invention was initially developed for the specific purpose of increasing the quantity and quality of biogas produced by activity of methanogens on waste materials in an anaerobic digester, it should be obvious to those skilled in the art of bioconversion processes that the general process of the described invention can be used to achieve other useful results through bioconversion. It is in principle applicable to a wide range of other bioconversion processes that use microorganisms (for instance, bacteria, yeast, fungi, algae, or genetically engineered microorganisms) to process some substrate material in order to achieve a specific purpose—for example to produce a usable product (such as methanol, hydrogen, or other biofuels or biofuel precursors) or to destroy undesirable materials (such as organic pollutants in municipal waste water or fracking fluids).

The invention claimed is:

1. A process of increasing biogas (9) production, with high methane content, in anaerobic biodigestion plants, comprising:

a) obtaining from an anaerobic biodigester (3) a fraction of organic waste equal in weight to K times the weight of the daily organic waste load of the anaerobic biodigester (3), wherein the parameter K is a numeric value selected between $10^{-3}$ and $10^{-1}$, sending the fraction to one or more acceleration devices (4) within which a microenvironment ideal for the accelerated multiplication of methanogenic bacteria contained in the organic wastes (1) is established by introducing additives and nutrients, retaining the fraction in the one or more acceleration devices (4) until a final concentration (Cf) of the methanogenic bacteria in the fraction is equal to M times an initial concentration (Ci), wherein the parameter M is a numeric value selected between $10^3$ and $10^8$;

b) as soon as said final concentration (Cf) is obtained in the fraction, directing said fraction from the acceleration device (4) back to the anaerobic biodigester (3); and c) successively repeating steps a) and b).

2. The process according to claim 1, wherein the acceleration device (4) includes:

at least one watertight tank (41) within which the fraction of organic waste withdrawn from the anaerobic digester (3) is treated to accelerate multiplication of methanogen concentrations to reach the final concentration Cf;

means (42) for mixing, withdrawal from the anaerobic digester (3), and re-introduction to the anaerobic digester (3) of a fraction of organic waste equal in weight to K times the weight of the daily organic waste load of the anaerobic biodigester;

means for the temperature control (43) of the environment within the watertight tank;

means (44) for the introduction of additives and nutrients to the watertight tank;

monitoring means (45) including monitoring sensors for measurement and analysis of temperature (T), pressure (P), percentage of methane (CH4), biogas flow (biogas), ppm of carbon, nitrogen and phosphorus (C:N:P), acid-basic degree (pH), electrical conductivity (mS), redox (Rdx) and turbidity (TU) within the watertight tank;

means for biological sampling and analysis (46) able to measure the development of bacteria in materials being processed within the watertight tank;

means for introduction of chemical substances for pH control (47) of the environment within the watertight tank;

a methane storage tank (48);

means of analysis to identify optimal combinations of parameters for accelerating production of the methanogenic bacteria through analysis of data from operations of the means for the temperature control (43), means (44) for the introduction of additives and nutrients, monitoring means (45), means for biological sampling and analysis (46), and means for introduction of chemical substances for pH control (47); and means for sending data regarding the optimal parameters to the control system of the anaerobic biodigester (3).

3. The process according to claim 2, further comprising: introducing methane into the watertight tank of the acceleration device (4) from methane storage tank (48) and bubbling it through the material being processed in the watertight tank.

4. The process according to claim 1, wherein the anaerobic biodigester (3) includes an inlet section, through which the daily organic waste load of the anaerobic biodigester (3) is transported into the anaerobic biodigester (3), and from which the fraction of organic waste equal in weight to K times the weight of the daily organic waste load of the anaerobic biodigester (3) is removed and sent to the one or more acceleration device (4) for treatment in the watertight tank, after which treatment, the fraction of organic waste having attained the final concentration (Cf) of the methanogenic bacteria, is removed from the watertight tank and is directed from the acceleration device (4), back to the anaerobic biodigester (3) through the same inlet section of the anaerobic biodigester (3).

5. The process according to claim 1, wherein the anaerobic biodigester (3) includes intermediate sections, through which the fraction of organic waste is directed from the acceleration device (4) back to the anaerobic biodigester (3) after the fraction of organic waste having the final concentration (Cf) of the methanogenic bacteria is obtained in the one or more acceleration device (4).

6. The process according to claim 5, wherein the fraction of organic waste equal in weight to K times the weight of the daily organic waste load of the anaerobic biodigester (3) is removed through the intermediate sections and sent to the one or more acceleration device (4) for treatment in the watertight tank, the fraction of organic waste is directed from the acceleration device (4) back to the anaerobic biodigester (3) through the intermediate sections after the fraction of organic waste having the final concentration (Cf) of the methanogenic bacteria is obtained in the one or more acceleration device (4).

7. A process of increasing biogas (9) production, with high methane content, in anaerobic biodigestion plants, comprising:

a) obtaining from an accumulation mixer/homogenizer (2) a fraction of organic waste equal in weight to K times the weight of the daily organic waste load of the anaerobic biodigester (3), wherein the parameter K is a numeric value selected between $10^{-3}$ and $10^{-1}$, sending the fraction to one or more acceleration devices (4) within which a microenvironment ideal for the accelerated multiplication of methanogenic bacteria contained in the organic wastes (1) is established by introducing additives and nutrients, retaining the fraction in the one or more acceleration devices (4) until a final concentration (Cf) of the methanogenic bacteria in the fraction is equal to M times an initial concentration (Ci), wherein the parameter M is a numeric value selected between $10^3$ and $10^8$;

b) as soon as said final concentration (Cf) is obtained in the fraction, directing said fraction from the acceleration device (4) back to the accumulation mixer/homogenizer (2) or to the anaerobic biodigester (3); and c) successively repeating steps a) and b).

8. The process according to claim 7, wherein the acceleration device (4) includes:

at least one watertight tank (41) within which the fraction of organic waste withdrawn from the anaerobic digester (3) is treated to accelerate multiplication of methanogen concentrations to reach the final concentration Cf;

means (42) for mixing, withdrawal from the anaerobic digester (3), and re-introduction to the anaerobic digester (3) of a fraction of organic waste equal in weight to K times the weight of the daily organic waste load of the anaerobic biodigester;

means for the temperature control (43) of the environment within the watertight tank;

means (44) for the introduction of additives and nutrients to the watertight tank;

monitoring means (45) including monitoring sensors for measurement and analysis of temperature (T), pressure (P), percentage of methane (CH4), biogas flow (biogas), ppm of carbon, nitrogen and phosphorus (C:N:P), acid-basic degree (pH), electrical conductivity (mS), redox (Rdx) and turbidity (TU) within the watertight tank;

means for biological sampling and analysis (46) able to measure the development of bacteria in materials being processed within the watertight tank;

means for introduction of chemical substances for pH control (47) of the environment within the watertight tank;

a methane storage tank (48);

means of analysis to identify optimal combinations of parameters for accelerating production of the methanogenic bacteria through analysis of data from operations of the means for the temperature control (43), means (44) for the introduction of additives and nutrients, monitoring means (45), means for biological sampling and analysis (46), and means for introduction of chemical substances for pH control (47); and means for sending data regarding the optimal parameters to the control system of the anaerobic biodigester (3).

9. The process according to claim 8, further comprising: introducing methane into the watertight tank of the acceleration device (4) from methane storage tank (48) and bubbling it through the material being processed in the watertight tank.

* * * * *